United States Patent [19]

Lorraine et al.

[11] Patent Number: 5,760,904
[45] Date of Patent: Jun. 2, 1998

[54] METHOD AND SYSTEM FOR INSPECTING A SURFACE OF AN OBJECT WITH LASER ULTRASOUND

[75] Inventors: Peter William Lorraine, Niskayuna; Ralph Allen Hewes, Burnt Hills, both of N.Y.

[73] Assignee: General Electric Company, Schenectady, N.Y.

[21] Appl. No.: 686,873

[22] Filed: Jul. 26, 1996

[51] Int. Cl.$^6$ ............................................. G01B 9/02
[52] U.S. Cl. ............... 356/360; 356/432 T; 356/345
[58] Field of Search .................................. 356/345, 349, 356/359, 360, 432 T

[56] References Cited

U.S. PATENT DOCUMENTS 5,546,187  8/1996  Pepper et al. ........................ 356/349

OTHER PUBLICATIONS

"Air–Coupled Piezoelectric Detection of Laser–Generated Ultrasound" by DA Hutchins, et al, IEEE Trans. On Ultrasonics, Ferroelectrics, & Frequency Control, vol. 41, No. 6, Nov. 1994 pp. 796–805.

"Differential Fibre–Optic Sensing of Laser–Generated Ultrasound" by BA Williams, et al, Electronic Letters, vol.31, No. 5, Mar. 1995 pp. 391–392.

"Laser–Based Ultrasound Arrays for Generation and Detection of Narrowband, Single Mode Lamb Waves", by RC Addison, Jr., et al, 1994 Ultrasonics Symposium, pp. 1201–1204.

"Lamb Wave Tomography" by DP Jansen, et al, 1990 Ultrasonics Symposium, pp. 1017–1020.

"Non–Contact Lamb Wave Tomography" by DA Hutchins, et al, 1992 Ultrasonics Symposium, pp. 883–886.

"Characterization and Imaging with Lamb Wave Lens at Gigahertz Frequencies" by A. Bozkurt, et al, 1994 Ultrasonics Symposium, pp. 1417–1420.

"Advances in Air Coupled NDE for Rapid Scanning Applications" by R. Farlow, et al, 1994 Ultrasonics Symposium, pp. 1099–1102.

"Three Dimensional Ultrasonic Imaging Employing a Time-–Domain Synthetic Aperture Focusing Technique" by J. Waszak, et al, IEEE Transactions On Instrumentation and Measurement, vol. 39, No. 2, Apr. 1990, pp. 441–444.

"Improved Imaging with Multi–Saft" by M. Lorenz, et al, 1990 Ultrasonics Symposium, pp. 1123–1128.

U.S. Patent Application, "Method and System for Laser Ultrasonic Imaging of an Object" by Peter W. Lorraine, et al, Ser. No. 08/627670 (Attorney Docket RD-24,725) Filed Apr. 1, 1996.

*Primary Examiner*—Frank G. Font
*Assistant Examiner*—Robert Kim
*Attorney, Agent, or Firm*—David C. Goldman; Marvin Synder

[57] ABSTRACT

The present invention discloses a method and system for inspecting a surface of an object with laser ultrasound. In the present invention, the surface is scanned with a source laser emitting a laser beam at a plurality of scanning positions. The emitted laser beam generates surface or Lamb waves at the plurality of scanning positions and transmits the waves throughout the surface. The surface of the object is scanned with a detector laser emitting a laser beam onto the object surface at the plurality of scanning positions. Surface displacement produced by the waves reflected from the surface is detected with a detector at each scanning position. The detected displacement at each scanning position contains signals representing a laser ultrasound waveform data set corresponding to a two-dimensional surface region along the object. The laser ultrasound waveform data sets at each scanning position are processed with a synthetic aperture focusing technique in order to generate high resolution images. The images are then inspected for defects that include cracks, disbonds, and corrosion.

14 Claims, 5 Drawing Sheets

METHOD AND SYSTEM FOR INSPECTING A SURFACE OF AN OBJECT WITH LASER ULTRASOUND

BACKGROUND OF THE INVENTION

The present invention relates generally to the nondestructive evaluation, and more particularly to laser ultrasound inspection of engineering materials with surface and Lamb waves and a synthetic aperture focusing technique.

Within the aerospace industry, inspection of engineering materials has extreme importance in assuring continued performance of aging structures. For example, aircraft skins are frequently made from curved sheets of metal riveted to adjoining panels and supporting structure. As the aircraft ages, the aircraft skins need to be inspected for cracks, disbonds, corrosion, and other defects to insure safe operation. Generally, the inspection of the aircraft skins is over a large area. Frequently, the aircraft skins are inspected with conventional piezoelectric methods. However, inspecting large areas of curved structures such as aircraft skins with piezoelectric methods is time consuming. In order to achieve high spatial resolution, piezoelectric methods frequently require immersion focusing, which necessitates either a water jet or a trapped pool of water under a transducer. In either case, the water stream usually enters unpainted or stripped surfaces through the rivets or joints and compounds any corrosion.

In order to overcome some of the problems associated with the piezoelectric methods, laser ultrasound has been used to inspect aircraft skins. Laser ultrasound involves the generation or detection of ultrasound in materials with lasers. Generally, in laser ultrasonic inspection of aircraft skins, a source laser irradiates the surface of an aircraft skin at a particular point with laser beams. Ultrasonic waves may be generated by laser beams either by non-destructive local heating of the surface to create expansion and a strain wave (i.e., thermoelastic generation) or by increasing the amplitude of the beams to vaporize a small amount (e.g., <1 micron) of the aircraft skins to form a plasma that strikes the surface like a hammer (i.e., ablation generation). The ultrasonic waves propagate throughout the surface of the skin and are reflected back to the point on the surface. As the reflected ultrasonic waves return to the point on the surface of the skin, an interferometric detector is used to detect either displacement at the point or ultrasonic wave velocity by simultaneously irradiating the point on the surface with a laser beam. The detected displacement or velocity signals are then used to generate an image of the material. A more detailed discussion on laser ultrasonics is provided in *Laser Ultrasonics-Techniques and Applications* by C. B. Scruby and L. E. Drain (IOP Publishing Ltd., 1990), which is incorporated herein by reference.

Laser ultrasound has been generally unsuccessful in inspecting the aircraft skins because of local surface optical quality variations and sensitivity. In particular, the laser detector is unable to focus and therefore identify the exact spatial location of any reflectors within the material which give rise to the detected signals. The resolution is poor because the laser detector is generally sensitive to the normal component of motion and does not differentiate between different directions of arrival of the reflected ultrasonic wave. Present aircraft skin laser ultrasound inspection schemes achieve spatial resolution by using only the signal from the immediate region around the generation spot; signals propagating larger distances through the aircraft skin are ignored. As a consequence, these schemes are sensitive to local variations in optical finish such as paint or dirt, which give rise to signals difficult to distinguish from defects. Attempts to overcome the poor resolution have used patterns of light such as lines, rings, arcs, or discrete beams at multiple locations. Rings and lines focus moderately well over short distances but again are sensitive to local variations in optical finish. Arrays of sources have only modest surface directionality due to the limited number of sources available.

SUMMARY OF THE INVENTION

Therefore, it is a primary objective of the present invention to provide a method and system for inspecting engineering materials such as aircraft skins or aircraft engine components with laser ultrasound and to generate focused images with high resolution.

Another object of the present invention is to apply synthetic aperture focusing techniques to detected laser waveform data in order to attain focused images across a surface or throughout a volume.

Still another object of the present invention is to use surface or Lamb waves with the synthetic aperture focusing techniques to generate focused images across a surface or throughout a volume.

A further object of the present invention is to use knowledge of the dispersion relation for Lamb waves to perform frequency based synthetic aperture imaging.

Yet another object of the present invention is to use laser ultrasound to inspect aircraft skins or other structures for surface cracks, corrosion, attachment to other structures such as engine components, and other defects.

Still another object of the present invention is to employ temporally or spatially modulated sources with the synthetic aperture focusing technique to enhance detection.

Thus, in accordance with the present invention, there is provided a method and system for inspecting a surface of an object with laser based ultrasound. In the present invention, the surface is scanned with a source laser emitting a laser beam at a plurality of scanning positions. The emitted laser beam generates ultrasonic sound waves at the plurality of scanning positions and transmits the ultrasonic sound waves throughout the surface. The surface of the object is scanned with a detector laser emitting a laser beam onto the object surface at the plurality of scanning positions. Surface displacement produced by ultrasonic sound waves reflected from the surface is detected with a detector at each scanning position. The detected displacement at each scanning position contains signals representing a laser ultrasound waveform data set corresponding to a two-dimensional surface region along the object. The laser ultrasound waveform data sets at each scanning position are processed with a synthetic aperture focusing technique. In particular, the laser ultrasound waveform data sets are coherently summed along a time of flight locus curve to form an image of the two-dimensional surface region along the object.

While the present invention will hereinafter be described in connection with a preferred embodiment and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
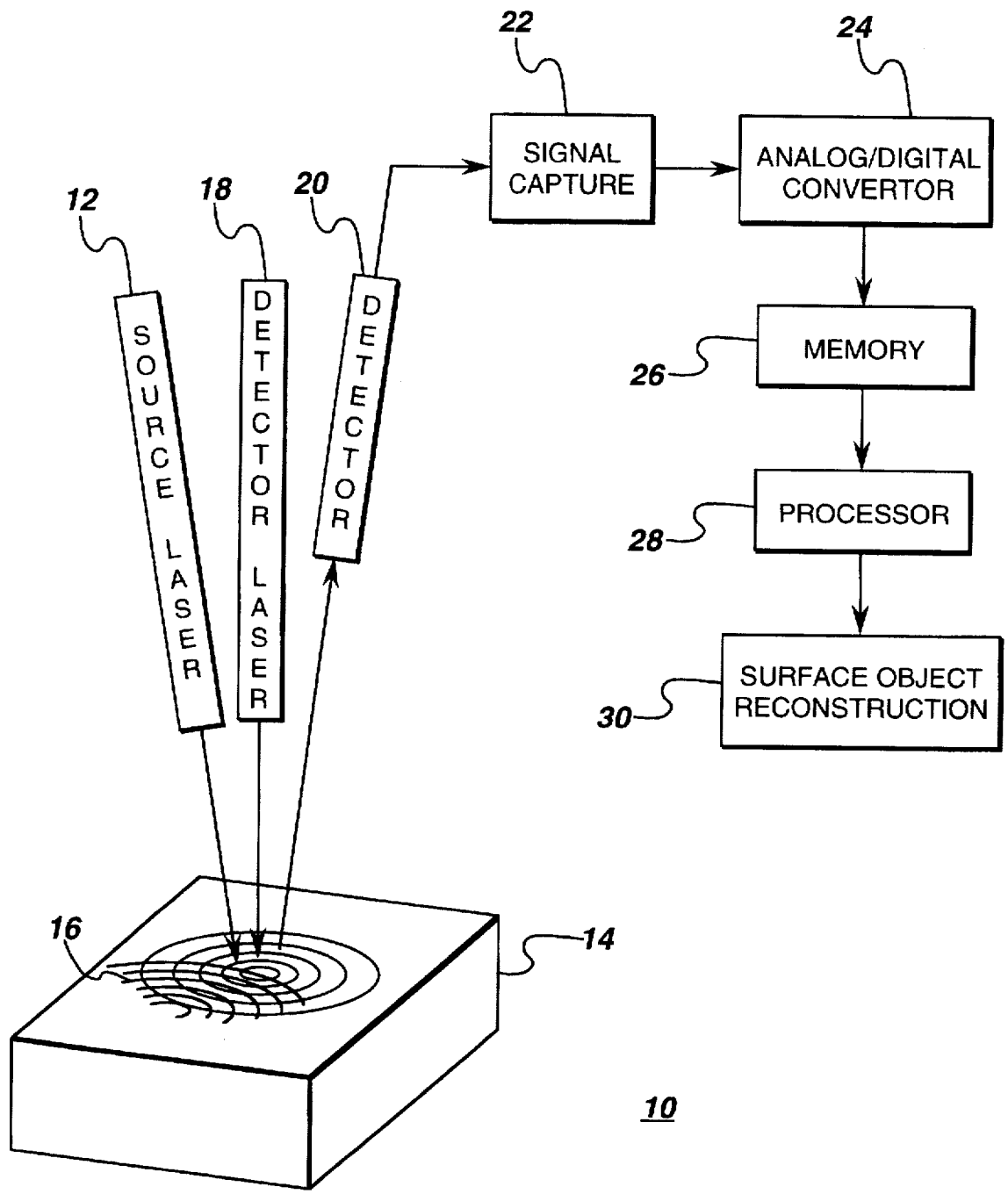
FIG. 1 shows a block diagram of a laser ultrasonic inspection system according to the present invention.

FIG. 1 shows a block diagram of a laser ultrasonic inspection system 10 used in the present invention. In the laser ultrasonic inspection system 10, a source laser 12 is scanned over the surface of an object 14. The object may be an engineering material such as a metal aircraft skin or any comparable structure. The source laser 12 irradiates the object 14 with a laser beam along its surface at a plurality of scanning positions. The laser beam generated from the source laser 12 has a high energy appropriate to the inspection, but generally is less than $5 \times 10^8$ W/cm$^2$. Ultrasonic waves are generated by laser beams either by nondestructive local heating of the surface to create expansion and a strain wave or by increasing the amplitude of the beams to vaporize a small amount (e.g., <1 micron) of material to form a plasma that strikes the surface like a hammer. In the illustrative embodiment, the generated ultrasonic waves are either surface or Lamb waves. The laser source spot size and shape will influence the ultrasound beam spread in the object and should be tailored to match the desired aperture size and detection distance. The spot energy may also be adjusted to vary the angular spread of ultrasound energy. In addition, more complex temporal and spatial modulation of the source laser spot may also be incorporated to enhance performance. The generated ultrasonic waves propagate throughout the surface of the object 14 and are reflected back to the to the scanning position by a defect 16 located along the surface. As the reflected ultrasonic waves return to the scanning position, a detection laser 18 is used to detect either displacement at the surface or ultrasonic wave velocity by simultaneously irradiating the surface with a laser beam. The laser beam generated from the detection laser 18 has line width, stability, and fluence suitable for interferometric detection. A detector 20, typically a sensitive interferometric detector, detects and amplifies the displacement or velocity signals and outputs the signals to a signal capture 22. The amplified signals represent a laser ultrasonic waveform data set corresponding to a two-dimensional surface region along the object 14. These signals are then digitized by an A/D converter 24 and stored in a memory 26. The laser ultrasonic waveform data stored in the memory are processed by a processor 28. The processor using the technique of the present invention, which is described later in further detail, reconstructs a surface image of the object that is displayed on a display 30.

Figure 2:
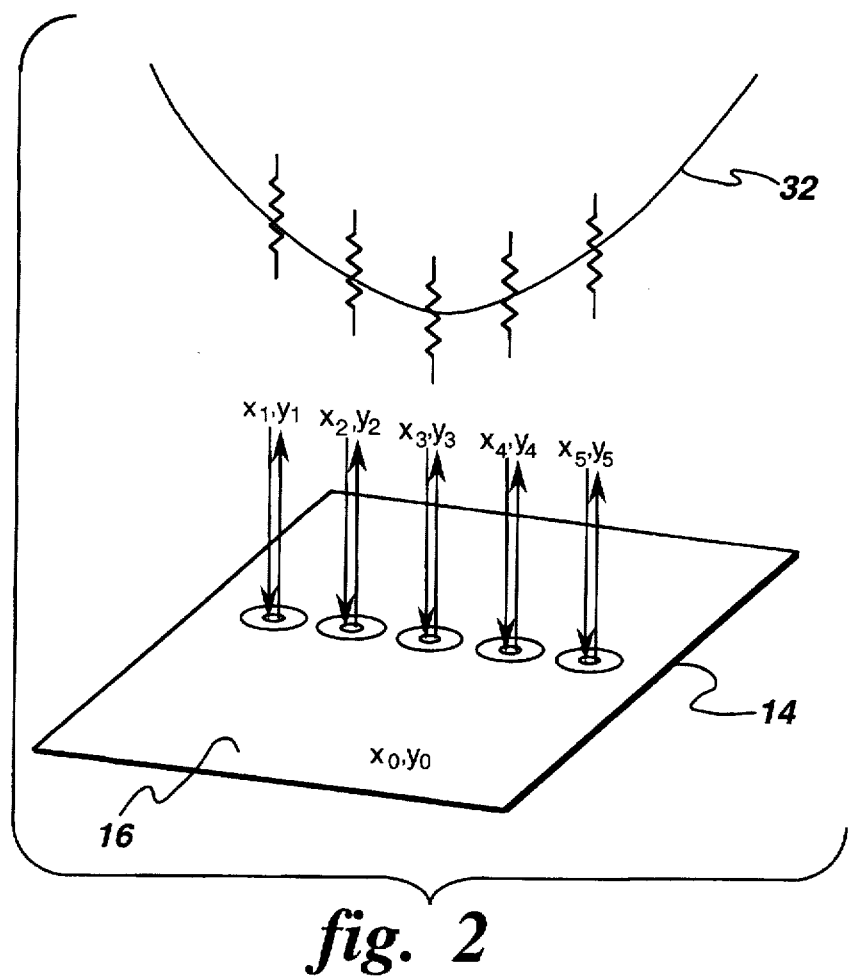
FIG. 2 shows a schematic diagram of image reconstruction for the laser ultrasonic inspection system using a synthetic aperture focusing technique.

FIG. 2 shows a schematic diagram of image reconstruction for the laser ultrasonic inspection system 10 using a synthetic aperture focusing technique (SAFT). In FIG. 2, the detector laser 18 and detector 20 are scanned linearly in the x-direction over the surface of object 14. At each spatial position, the detector laser 18 irradiates the surface of the object 14 with a laser beam to detect the displacement of the ultrasonic waves reflected from within the object. In FIG. 2, the reflected ultrasonic waves are caused by reflectors 16 located within the object 14. In the illustrative embodiment, the reflectors are defects that include cracks, corrosion, attachments to other structures, scratches, disbonds, and other defects. The detector 20 detects the displacement or velocity at the surface of the object at each scanning position. In the present invention, the laser ultrasonic waveform data corresponds to displacement. In the illustrative embodiment, the detector 20 receives a back scattered signal (i.e., an A scan) at a constant measurement position $\Delta x$ and $\Delta y$. The top portion of FIG. 2 shows the relationship between the detector laser 18 and the detector 20 on the surface of the object and the acoustic reflector 16 ($x_0$, $y_0$) in the part that has a reflectivity $r(x_0, y_0)$. In particular, the time of flight $t(x)$ between the point of focus of the detector laser 18 and the detector 20 and the acoustic reflector is represented by a curve 32. At the first measurement position $\Delta x$, the acoustic reflector ($x_0$, $y_0$) is within range of the generated ultrasonic sound wave and therefore a back scatter signal is detected by the detector laser 18 and the detector 20. In the next three measurement positions, the acoustic reflector ($x_0$, $y_0$) is within range of the generated ultrasonic sound wave and back scatter signals are detected by the detector laser 18 and the detector 20. At the last measurement position, the acoustic reflector ($x_0$, $y_0$) is within the range of the generated ultrasonic sound wave and a back scatter signal is detected by the detector laser 18 and the detector 20. Sound energy propagating in a surface plane attenuates much more gradually than sound energy in a volume. For this reason, the maximum distance for surface points to be within the source/detection range is much greater than in a volume inspection. The image of the acoustic reflector is produced by coherently summing up the detected back scatter signals.

In one embodiment of the present invention, the above-described SAFT procedure is able to detect front surface and rear surface defects in aircraft skins and engine components such as cracks, corrosion, attachments to other structures, scratches, and disbonds, by using surface or Rayleigh waves. Surface waves typically extend down into a material at a distance on the order of twice the surface wavelength. For example, on titanium, the surface wave travels at approximately 2.9 mm/µs. At 3 MHz, the surface wave samples a depth to 2 mm. This characteristic permits inspection below the surface of the aircraft skin into "blind zones", which are not normally able to be inspected with eddy current techniques or volumetric piezoelectric immersion ultrasound. The SAFT reconstruction approach for surface inspection is much simpler than for volume inspection as only a single plane is reconstructed, while for a volume reconstruction, planes are required at each depth of interest. In particular, the computation can be performed by off-the-shelf personal computers in real time.

Figure 3:
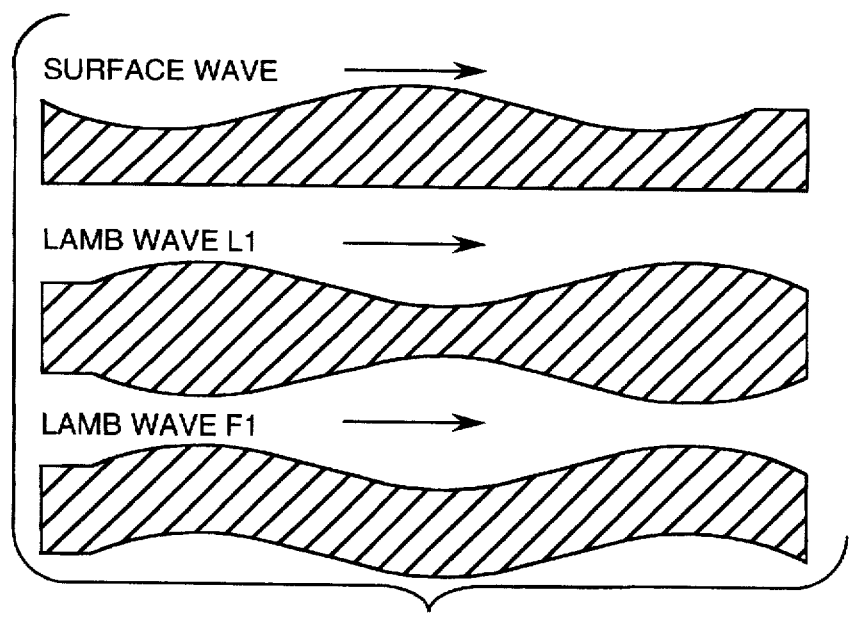
FIG. 3 shows the differences between surface waves and Lamb waves.

In another embodiment of the present invention, the above-described SAFT procedure is able to detect defects in the aircraft skins such as cracks, corrosion, attachments to other structures, scratches, and disbonds, by using Lamb waves. Lamb waves are generated when the object is less than several wavelengths thick, such that surface waves engage the object at its opposite face. Lamb waves are dispersive, which means that different frequency components propagate with different sound velocities determined by elastic constants and geometry. This dispersive characteristic makes Lamb waves sensitive to variations in thickness, and thus suitable for detecting corrosion in the aircraft skins. FIG. 3 shows the differences between surface waves and Lamb waves.

By using either an empirical or theoretical model of the Lamb wave in the above-described SAFT procedure, it is possible to image all frequency components to enhance resolution. In contrast to other approaches, such as using rings of light to produce converging sound beams, in the present invention the imaging aperture is formed across many surface points and is not as sensitive to local variations. For example, a source detection location $x_i, y_i$, a detected time varying waveform $u(x_i, y_i, t)$ and an image location X,Y, can be used to obtain a frequency varying waveform defined by:

$$U(x_i, y_i, \omega) = \int_{-\infty}^{\infty} e^{i\omega t} u(x_i, y_i, t) dt, \quad (1)$$

wherein $U(x_i, y_i, \omega)$ is the frequency varying waveform. Because reconstruction can be performed easily in the frequency domain, the computational penalty is minimal. The change of phase for a given frequency associated with travel from the source laser to a reflector and back to the source laser is defined by:

$$\Delta\Phi(X, Y, x_i, y_i, \omega) = \omega t = 2\omega \frac{\sqrt{(X-x_i)^2 + (Y-y_i)^2}}{c(\omega)}, \quad (2)$$

wherein $\Delta\Phi$ is the change of phase and c is the speed of light. The frequency components are summed to "focus" at the image location by:

$$I(X, Y, \omega) = \sum_i U(x_i, y_i, \omega) e^{-i\omega\Delta\Phi(X, Y, x_i, y_i, \omega)}, \quad (3)$$

wherein $I(X, Y, \omega)$ is the image amplitude at an image point. The use of a specific velocity or dispersion relation enables the present invention to create a coherent image for a given mode. Another mode, if present, will have a different dispersion relation which will lead to dephasing of echoes propagating at different velocities. The artifacts usually associated with other modes are suppressed through this processing and give rise to an increased background. Sources which selectively generate the desired mode will tend to give higher contrast images, as will selective detectors.

Figure 4:
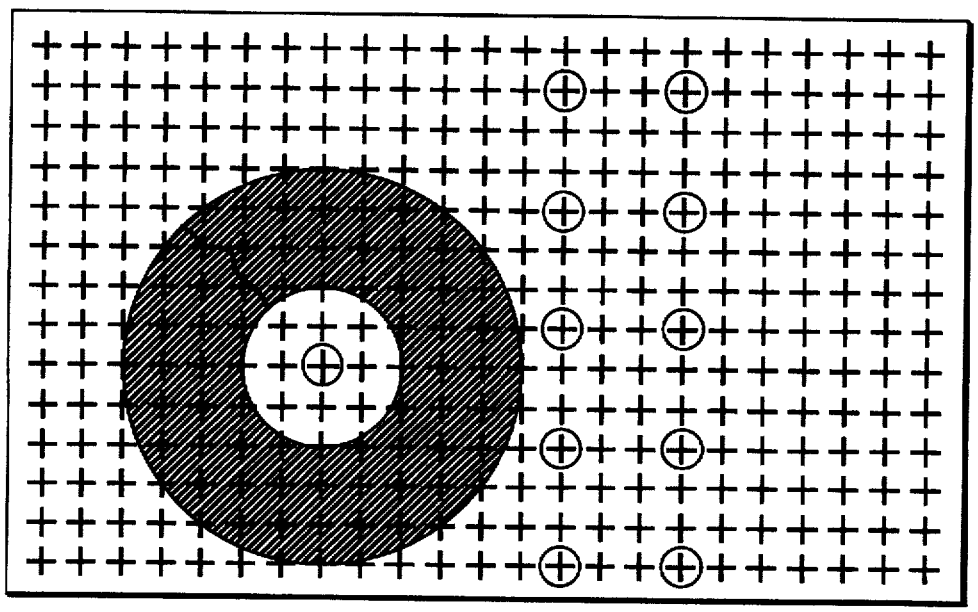
FIG. 4 shows a schematic of laser ultrasound inspection of an aircraft skin according to the present invention.

FIG. 4 shows one embodiment of a laser ultrasound inspection of an aircraft skin according to the present invention. In particular, the generation and detection of beams are scanned over the surface of the aircraft skin at each scanning location designated with a "+". The shaded region indicates a reconstruction aperture formed from the SAFT procedure. An image for the image points within the aperture is generated from all of the scanning locations "+" within the shaded aperture region. Similar apertures are generated for all desired image points. Source/detector locations that are remotely located from the image point do not contribute much information. Similarly, in some cases the detector response may be dominated by source effects for a short time after generation. In FIG. 4, the aperture includes points beyond a certain distance from the image point. Apertures may be generated to view cracks from arbitrary orientations to enhance detection.

Figure 5A:
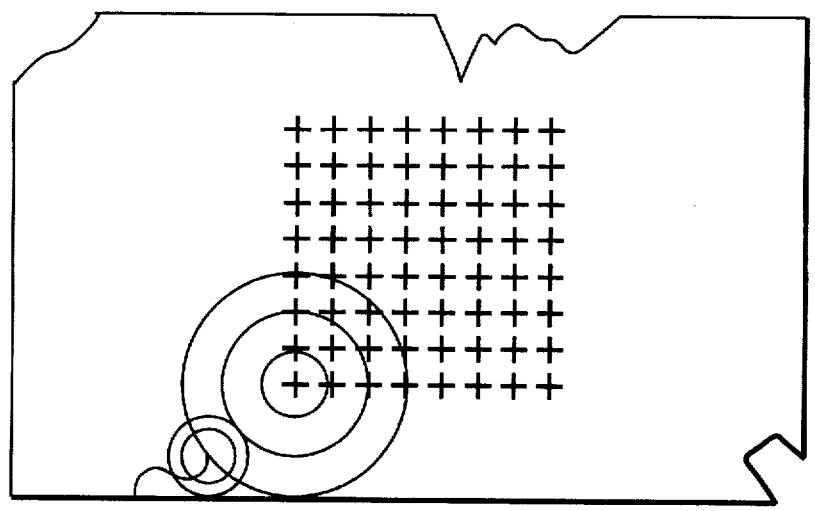
FIGS. 5a–5c show a comparison of the laser ultrasound inspection procedure of the present invention with conventional inspection approaches.
Figure 5B:
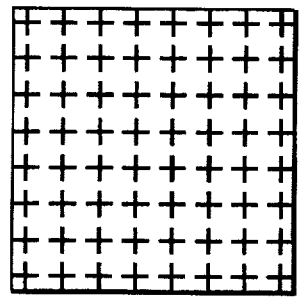
Figure 5C:
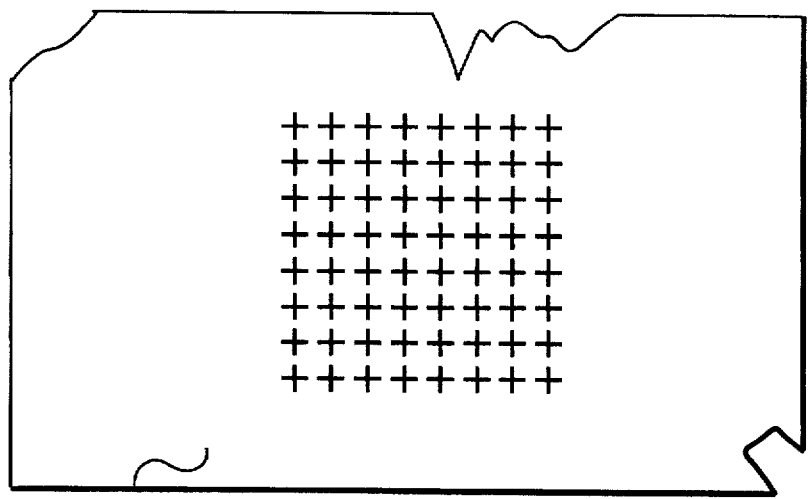

One of the advantages of the present invention is illustrated in FIGS. 5a-5c. More specifically, the present invention is able to reconstruct a bigger part of the aircraft skin from only a scan of a limited area. FIGS. 5a-5b shows that only defects in the scanned area are capable of being imaged with conventional procedures, whereas FIG. 5c shows that defects can be imaged in the entire region of interest from only a limited scan with the present invention. Other advantages of the present invention are that it has the capability to rapidly scan curved aircraft skins or other parts, it produces high resolution images by using surface or Lamb wave imaging with dispersion compensation, and that it has a lack of sensitivity to local surface finish because of averaging effect across the aperture. A more detailed discussion on the lack of sensitivity to local surface finish is provided in U.S. Ser. No. 08/627670, entitled Method And System For Laser Ultrasonic Imaging Of An Object, which is incorporated herein by reference.

Figure 6A:
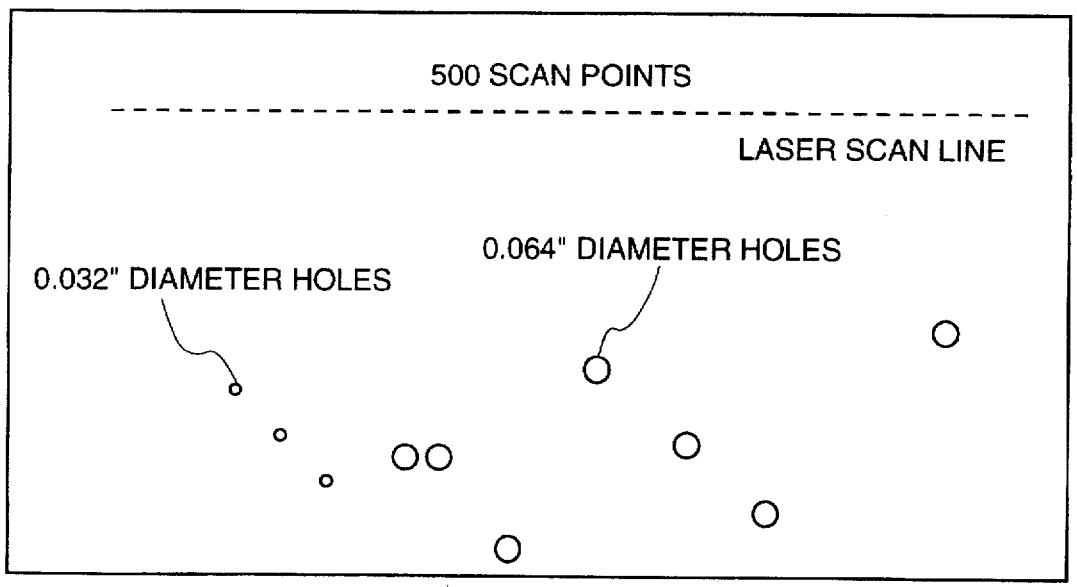
FIGS. 6a–6b show a reduction to practice of the present invention demonstrating the ability to image an extended surface area of an aluminum plate from limited scan data.
Figure 6B:
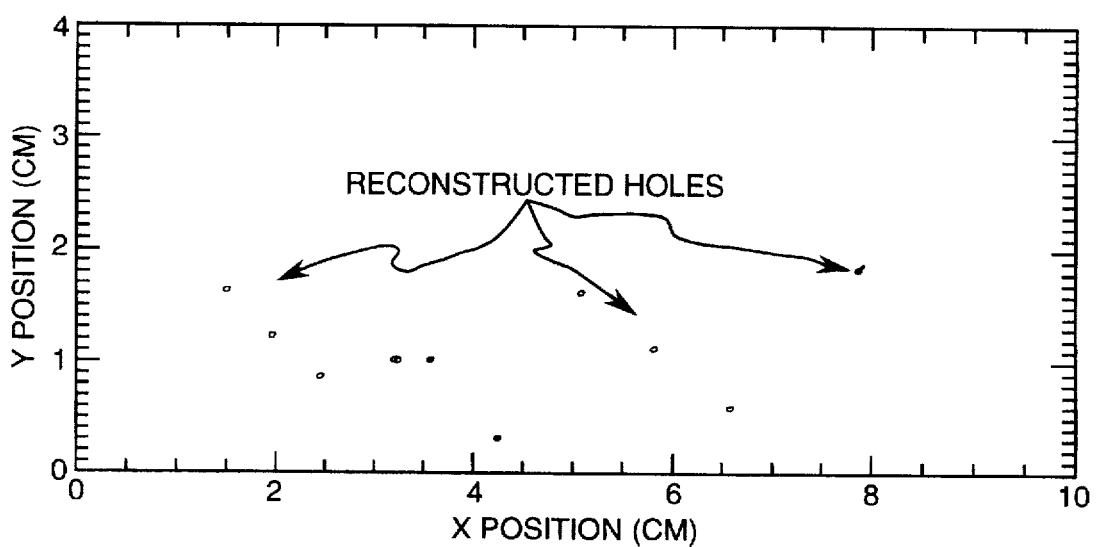

The present invention's ability to produce images of areas beyond the scan area has been reduced to practice and is shown in FIGS. 6a-6b. A part consisting of an aluminum plate with a pattern of surface breaking holes of diameter 0.032" and 0.064" was fabricated and is shown in FIG. 6a. The source laser 12, detector laser 18, and detector 20 were scanned to acquire data at 500 points along a single scan line across the surface of the plate (FIG. 6a). FIG. 6b shows a contour map of the reconstructed image of the surface of the plate. The processing clearly resolves all of the holes. By reconstructing a single scan line to display the entire surface, the effective area scan rate is increased enormously.

It is therefore apparent that there has been provided in accordance with the present invention, a method and system for inspecting a surface of an object with laser ultrasound that fully satisfy the aims and advantages and objectives hereinbefore set forth. The invention has been described with reference to several embodiments, however, it will be appreciated that variations and modifications can be effected by a person of ordinary skill in the art without departing from the scope of the invention. For example, longitudinal or shear waves may be used to inspect and image the object for providing more accurate estimates of thickness in critical areas.

The invention claimed is:

1. A method for inspecting a surface of an object with laser based ultrasound, comprising the steps of:
    scanning the surface with a source laser emitting a laser beam at a plurality of scanning positions, the emitted laser beam generating ultrasonic sound waves at the plurality of scanning positions and transmitting the ultrasonic sound waves throughout the surface;
    scanning the surface of the object with a detector laser emitting a laser beam onto the object surface at the plurality of scanning positions;
    detecting surface displacement produced by ultrasonic sound waves reflected from the surface with a detector at each scanning position, the detected displacement at each scanning position containing signals representing a laser ultrasound waveform data set corresponding to a two-dimensional surface region along the object; and
    processing the laser ultrasound waveform data sets at each scanning position with a synthetic aperture focusing technique wherein the laser ultrasound waveform data sets are coherently summed along a time of flight locus curve forming an image of the two-dimensional surface region along the object.

2. The method according to claim 1, further comprising the step of displaying the image of the object.

3. The method according to claim 2, further comprising the step of evaluating the image of the object for defects comprising corrosion, cracks, and disbonds.

4. The method according to claim 1, wherein the generated ultrasonic waves comprise Lamb waves.

5. The method according to claim 4, wherein the image is formed by using dispersion compensation.

6. The method according to claim 1, wherein the generated ultrasonic waves comprise surface waves.

7. The method according to claim 1, further comprising the step of using temporally or spatially modulated sources to enhance detection.

8. A system for laser ultrasonic inspecting a surface of an object, comprising:
- a source laser for scanning the surface, the source laser emitting a first laser beam at a plurality of scanning positions along the surface, the first emitted laser beam generating ultrasonic sound waves at the plurality of scanning positions and transmitting the ultrasonic sound waves throughout the surface;
- a detector laser for scanning the surface, the detector laser emitting a second laser beam onto the surface at the plurality of scanning positions;
- a detector for detecting surface displacement produced by ultrasonic sound waves reflected from the surface, the detected displacement at each scanning position containing signals representing a laser ultrasonic waveform data set corresponding to a two-dimensional surface region along the object; and means for processing the laser ultrasonic waveform data sets at each scanning position with a synthetic aperture focusing technique wherein the laser ultrasonic data sets are coherently summed along a time of flight locus curve forming an image of the two-dimensional surface region along the object.

9. The system according to claim 8, further comprising a display for displaying the image of the object.

10. The system according to claim 9, further comprising means for evaluating the image of the object for defects comprising corrosion, cracks, and disbonds.

11. The system according to claim 8, wherein the generated ultrasonic waves comprise Lamb waves.

12. The system according to claim 11, wherein the image is formed using dispersion compensation.

13. The system according to claim 8, wherein the generated ultrasonic waves comprise surface waves.

14. The system according to claim 8, further comprising means for enhancing detection temporally or spatially.

* * * * *